(12) United States Patent
Wang et al.

(10) Patent No.: US 9,131,862 B2
(45) Date of Patent: Sep. 15, 2015

(54) METHOD FOR EXTRACTING ARTERIAL INPUT FUNCTION AND APPLICATION THEREOF TO DYNAMIC CONTRAST ENHANCED MAGNETIC RESONANCE IMAGING

(71) Applicant: CHANG GUNG UNIVERSITY, Tao-Yuan (TW)

(72) Inventors: Jiun-Jie Wang, Guishan Township, Taoyuan County (TW); Yu-Chun Lin, Guishan Township, Taoyuan County (TW); Tsung-Han Chan, Hsinchu (TW); Chong-Yung Chi, Baoshan Township, Hsinchu County (TW); Shu-Hang Ng, Guishan Township, Taoyuan County (TW); Yau-Yau Wai, Guishan Township, Taoyuan Couny (TW)

(73) Assignee: Chang Gung University, Tao-Yuan (TW)

(*) Notice: Subject to any disclaimer, the term of this patent is extended or adjusted under 35 U.S.C. 154(b) by 261 days.

(21) Appl. No.: 13/781,059

(22) Filed: Feb. 28, 2013

(65) Prior Publication Data
US 2014/0241604 A1 Aug. 28, 2014

(30) Foreign Application Priority Data
Aug. 30, 2012 (TW) .............................. 101131482 A

(51) Int. Cl.
*G01R 33/563* (2006.01)
*G06T 7/00* (2006.01)
(Continued)

(52) U.S. Cl.
CPC ............ *A61B 5/0263* (2013.01); *G01R 33/563* (2013.01); *G06T 7/0016* (2013.01);
(Continued)

(58) Field of Classification Search
CPC .................... A61B 5/02; A61B 5/055; G06T 2207/10088; G06T 2207/10096; G01R 33/563; G01R 33/5635; G01R 33/20
USPC .................................................. 382/128, 131
See application file for complete search history.

(56) References Cited

U.S. PATENT DOCUMENTS

| 2011/0044524 A1* | 2/2011 | Wang et al. ................... 382/131 |
| 2013/0011037 A1* | 1/2013 | Shi et al. ....................... 382/131 |

OTHER PUBLICATIONS

Carroll, et al. "Automatic Calculation of the Arterial Input Function for Cerebral Perfusion Imaging with MR Imaging." Radiology 227.2 (2003): 593-600. Print.*

(Continued)

*Primary Examiner* — Michael A Newman
(74) *Attorney, Agent, or Firm* — Muncy, Geissler, Olds & Lowe, P.C.

(57) ABSTRACT

The present invention discloses a method for extracting AIF and an application thereof to DCE-MRI. The method comprises steps: contacting a target tissue with a contrast agent to obtain a plurality of images; using the plurality of images to work out the tissue concentration curve of the contrast agent in each voxel; calculating the purity of the tissue concentration curve of each voxel according to the tissue concentration curves; and extracting the voxel having the highest purity as the optimized arterial location; and extracting the tissue concentration curve of the voxel having the highest purity as the arterial input function. The extracted AIF is applied to a pharmacokinetic model to obtain associated pharmacokinetic parameters. The present invention not only improves the accuracy and reliability of the derived quantitative indexes but also promotes the efficiency of the quantitative analysis.

13 Claims, 11 Drawing Sheets

(51) Int. Cl.
   *A61B 6/03* (2006.01)
   *A61B 5/02* (2006.01)
   *A61B 5/026* (2006.01)
   *A61B 6/00* (2006.01)
(52) U.S. Cl.
   CPC .......... *A61B 6/032* (2013.01); *A61B 6/486* (2013.01); *A61B 6/507* (2013.01); *A61B 6/5217* (2013.01); *G06T 2200/04* (2013.01); *G06T 2207/10076* (2013.01); *G06T 2207/10081* (2013.01); *G06T 2207/10096* (2013.01); *G06T 2207/10104* (2013.01); *G06T 2207/30104* (2013.01)

(56) References Cited

OTHER PUBLICATIONS

Zhu, et al. "Quantification of Endothelial Permeability Leakage Space, and Blood Volume in Brain Tumors Using Combined T1 and T2* Contras-Enhanced Dynamic MRI Imaging." Journal of Magnetic Resonance Imaging 11 (2000): 575-85. Print.*
Ferreira, et al. "Arterial Input Function Placement for Accurate CT Perfusion Map Construction in Acute Stroke." AJR Am J Roentgenol. 194.5 (2010): 1330-336. Print.*
Yee, et al. "Quantitative Measurement of Oxygen Metabolic Rate in the Rat Brain Using MicroPET Imaging of Briefly Inhaled O-labelled Oxygen Gas." Nuclear Medicine Communications 27.7 (2006). Print.*
Chen, et al. "Automatic Determination of Arterial Input Function for Dynamic Contrast Enhanced MRI in Tumor Assessment." Medical image computing and computer-assisted intervention : MICCAI . . . International Conference on Medical Image Computing and Computer-Assisted Intervention 11.Pt 1 (2008): 594-601. Print.*
Zhu, et al. "Automated Determination of Arterial Input Function for DCE-MRI of the Prostate." SPIE 7963, Medical Imaging 2011: Computer-Aided Diagnosis 7963 (2011): 1-7. Print.*
Parker, et al. "Automated Arterial Input Function Extraction for T1-Weighted DCE-MRI." Proc. Intl. Soc. Mag. Reson. Med. 11 (2003): 1264. Print.*
Schabel, et al. "A Model-constrainted Monte Carlo Method for Blind Arterial Input Function Estimation in Dynamic Contrast-enhanced MRI: II. In Vivo Results." Phys. Med. Biol. 55 (2010): 4807-823. Print.*
Cheng, Hai-Ling Margaret, PhD, "Investigation and Optimization of Parameter Accuracy in Dynamic Contrast-Enhanced MRI", Journal of Magnetic Resonance Imaging, (2008), pp. 736-743.
Yang, Cheng et al., "Multiple Reference Tissue Method for Contrast Agent Arterial Input Function Estimation", Magnetic Resonance in Medicine, (2007), pp. 1266-1275.
Murase, Kenya, "Efficient Method for Calculating Kinetic Parameters Using T1-Weighted Dynamic Contrast-Enhanced Magnetic Resonance Imaging", Manetic Resonance in Medicine, (2004), pp. 858-862.
Mouridsen, Kim et al., "Automatic Selection of Arterial Input Function Using Cluster Analysis", Magnetic Resonance in Medicine, (2006), pp. 524-531.
Yankeelov, Thomas E. et al., "Comparison of a Reference Region Model With Direct Measurement of an AIF in the Analysis of DCE-MRI Data", Magnetic Resonance in Medicine, (2007), pp. 353-361.
Sourbron, Steven et al., "Quantification of Cerebral Blood Flow, Cerebral Blood Volume, and Blood—Brain-Barrier Leakage with DCE-MRI", Magnetic Resonance in Medicine (2009), pp. 205-217.
Kjolby, Birgitte F. et al., "Analysis of Partial Volume Effects on Arterial Input Functions Using Gradient Echo: A Simulation Study",Magnetic Resonance in Medicine, (2009), pp. 1300-1309.
McGrath, Deirdre M. et al., "Comparison of Model-Based Arterial input Functions for Dynamic Contast-Enhanced MRI in Tumor Bearing Rats", Magnetic Resonance in Medicine (2009), pp. 1173-1184.
Bleeker, Egbert J.W. et al., "New Criterion to Aid Manual and Automatic Selection of the Arterial Input Function in Dynamic Susceptibility Contrast MRI", Magnetic Resonance in Medicine (2011), pp. 448-456.
Calamante, Fernando et al., "Bolus Delay and Dispersion in Perfusion MRI: Implications for Tissue Predictor Models in Stroke", Magnetic Resonance in Medicine, (2006), pp. 1180-1185.
Cho, Hyungjoon et al., "Imaging of the Tumor Microenvironment: Registered Dynamic Magnetic Resonance Imaging and Positron Emission Tomography Studies of a Preclinical Tumor Model of Tumor Hypoxia". Neoplasia Press (2009), pp. 247-259.
Roberts, Caleb et al., "Glandular Function in Sjo gren Syndrome: Assessment with Dynamic Contrast-enhanced MR Imaging and Tracer Kinetic Modeling—Initial Experience", Radiology, (2008), pp. 845-853.
Parker, Geoffrey J.M. et al., "MRIW: Parametric Analysis Software for Contrast enhanced Dynamic MR Imaging in Cancer", infoRAD, (1998), pp. 496-506.
Carroll, Timothy J. et al., :Automatic Calculation of the Arterial Input Function for Cerebral Perfusion Imaging with MR Imaging, Arterial Input Function for Assessment of Cerebral Blood Flow, (2003), pp. 593-599.
Tofts, Paul S., Dphil, "Modeling Tracer Kinetics in Dynamic GdIDTPA MR Imaging", JMRI, ( 1997), pp. 91-101.
Tofts, Paul S., Dphil, et al., "Estimating Kinetic Parameters From Dynamic Contrast-Enhanced T1-Weighted MRI of a Diffusable Tracer: Standardized Quantities and Symbols", Journal of Magnetic Resonance Imaging, (1999), pp. 223-232.
Yankeelov, Thomas E. et al., "Quantitative pharmacokientic analysis of DCE-MRI data without an arterial input function: a reference region model", Magnetic Resonance Imaging, (2005), pp. 519-529.
Zhu, X.P., MD, PhD, et al., "quantification of Endothelial Permeability, Leakage Space, and Blood Volume in Brain Tumors Using Combined T1 and T2* Contrast-Enhanced Dynamic MR Imaging", Journal of Magnetic Resonance Imaging, (2000), pp. 575-585.
Lin, Yu-Chun et al., "Blind Estimation of the Arterial Input Function in Dynamic Contrast-Enhanced MRI Using Purity Maximization", Magnetic Resonance in Medicine, (2012) pp. 1-12.

* cited by examiner

METHOD FOR EXTRACTING ARTERIAL INPUT FUNCTION AND APPLICATION THEREOF TO DYNAMIC CONTRAST ENHANCED MAGNETIC RESONANCE IMAGING

BACKGROUND OF THE INVENTION

1. Field of the Invention

The present invention relates to a method for extracting an arterial input function from dynamic medical imaging data, particularly to a method using a blind source separation algorithm to automatically extract an arterial input function closest to the ground-true arterial input function and the application thereof to dynamic contrast enhanced magnetic resonance imaging.

2. Description of the Related Art

Dynamic contrast-enhanced magnetic resonance imaging (DCE-MRI) is a non-invasive imaging tool for estimation of tissue physiological parameters, such as perfusion, capillary permeability, and the volume of extravascular-extracellular space. The conventional practice of DCE-MRI includes acquiring imaging immediately after contrast agent injection and using a pharmacokinetic model to quantitatively work out some indexes, such as the transfer rate constant ($K^{trans}$) from the intravascular system to the extravascular extracellular space (EES) or vice versa, the distribution volume (Ve) of the contrast agent in EES and the capillary plasma volume (Vp) of the contrast agent in EES, which are very useful in diagnosis and therapeutic estimation of vessel-related diseases, such as tumors and apoplexies.

The pharmacokinetic model requires the knowledge of the arterial input function (AIF). The accuracy of the derived kinetic parameters largely depends on AIF. However, there is still lacking a settled standard to obtain AIF for DCE-MRI. AIF is obtained via manual selection traditionally. However, manual selection is operator-dependent and apparently subjective. Further, the results estimated therefrom are susceptible to the partial volume effect outside the selected region. Parker et al. developed a population-averaged AIF, which is simple and convenient for clinical use. However it neglects individual variation in AIF and may output inaccurate estimation of quantitative parameters. (Refer to Parker G J, Roberts C, Macdonald A, Buonaccorsi G A, Cheung S, Buckley D L, Jackson A, Watson Y, Davies K, Jayson G C. Experimentally-derived functional form for a population-averaged high-temporal-resolution arterial input function for dynamic contrast-enhanced MRI. Magn Reson Med 2006; 56(5): 993-1000.) The reference region approach extracts the AIF by comparing the measured data in healthy tissues with the literature values. It is limited by the requirement of a well-characterized normal tissue within the FOV (Field Of View) and thus still has some problems to overcome.

Accordingly, the present invention proposes a method for extracting AIF and an application thereof to DCE-MRI to overcome the conventional problems and reduce the estimation error caused by the uncertainty of the conventional AIF extraction methods.

SUMMARY OF THE INVENTION

The primary objective of the present invention is to provide a method for extracting AIF and an application thereof to DCE-MRI, wherein a blind source separation (BSS) algorithm calculates the purities of voxels from the captured continuous imaging data to extract AIF by selecting the voxel time course with the highest purity, whereby the extracted AIF is closest to the true AIF, and whereby are increased the accuracies of the deduced quantitative indexes.

Another objective of the present invention is to provide a DCE-MRI method, which extracts the AIF closest to the truth from the imaging data to promote the efficiency of quantitative analysis of DCE-MRI and increase the reliability of the deduced indexes.

To achieve the abovementioned objectives, the present invention proposes a method for extracting AIF, which comprises steps: contacting a target tissue with a contrast agent to obtain plurality of images; using the plurality of images to work out the time intensity curve of the contrast agent in each voxel; calculating the purity of the time intensity curve of each voxel according to the time intensity curves; and extracting the time intensity curve of the voxel having the highest purity as the arterial input function.

The abovementioned plurality of images are obtained via MRI (Magnetic Resonance Imaging), CT (Computed Tomography), or PET (Positron Emission Tomography).

The present invention also proposes a DCE-MRI method, which comprises steps: contacting a target tissue with a contrast agent to obtain a plurality of images of MRI; using the plurality of images to work out the tissue concentration curve of the contrast agent in each voxel; calculating the purity of the tissue concentration curve of each voxel according to the tissue concentration curves; extracting the tissue concentration curve of the voxel having the highest purity as the arterial input function (AIF); applying the extracted AIF to a pharmacokinetic model to generate pharmacokinetic parameters for diagnosing vessel-related diseases or calculating the therapeutic effects of the vessel-related diseases.

The abovementioned pharmacokinetic parameters include the transfer rate constant ($K^{trans}$) from the intravascular system to the extravascular extracellular space (EES) or vice versa, the distribution volume (Ve) of the contrast agent in EES and the capillary plasma volume (Vp) of the contrast agent in EES. The abovementioned pharmacokinetic parameters may further include the cerebral blood flow (CBF), the cerebral blood volume (CBV), and the mean transit time (MTT).

Below, embodiments are described in detail in cooperation with the attached drawings to make easily understood the objectives, technical contents, characteristics and accomplishments of the present invention.

DETAILED DESCRIPTION OF THE INVENTION

In performing calculation of DCE-MRI, the adopted AIF would influence the quantitative parameters deduced through a mathematical model of pharmacokinetics. The present invention uses a BSS (Blind Source Separation) algorithm to work out the purity of each voxel from the imaging data generated in DCE-MRI. Then, the present invention automatically searches for the voxel having the highest purity as the optimized AIF. Thereby, the present invention can derive more accurate quantitative parameters from the pharmacokinetic model, i.e. the pharmacokinetic parameters.

Figure 1:
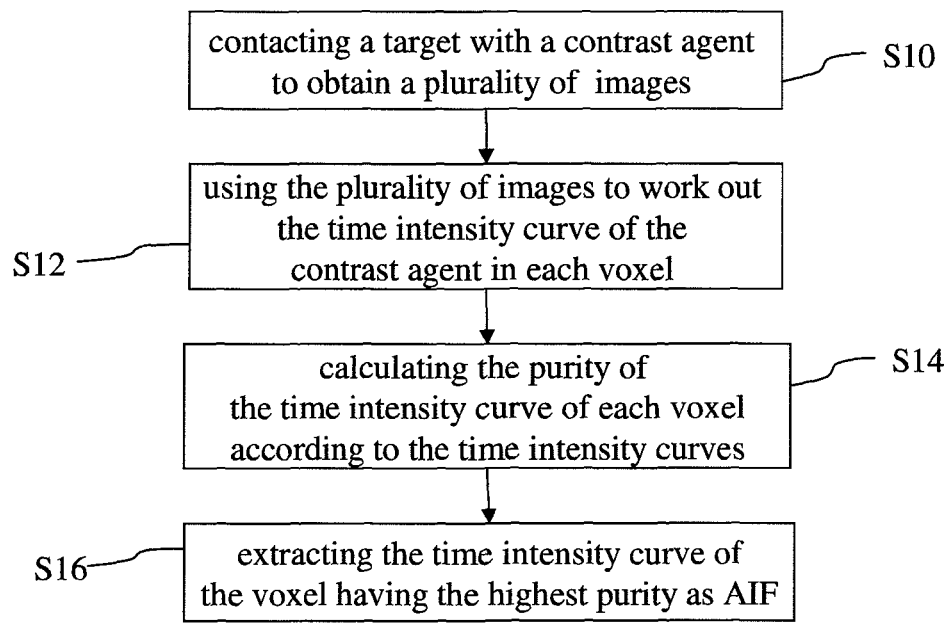
FIG. 1 shows a flowchart of a method for extracting AIF according to one embodiment of the present invention.

Refer to FIG. 1 showing a flowchart of a method for extracting AIF according to one embodiment of the present invention. The method of the present invention comprises Steps S10, S12, S14 and S16. In Step S10, inject or perfuse a contrast agent into a target tissue, and use MRI, CT, or PET to obtain a plurality of images. In Step S12, use the plurality of images, which are obtained while the blood carrying the contrast agent flows into and flows out from the target tissue, to acquire the time course curve of the tissue concentration of the contrast agent in each voxel, i.e. the time intensity curve, from the 3D data set of the concentration of the contrast agent in the target tissue. In Step S14, automatically use the time intensity curves to calculate the purity corresponding to the time intensity curve of each voxel in the 3D data set of the target tissue. The higher the purity, the less the partial volume effect. In Step S16, select the voxel having the highest purity as the optimized arterial location, and automatically extract the time intensity curve of the voxel as AIF. Therefore, the present invention can obtain the optimized AIF theoretically.

Figure 2:
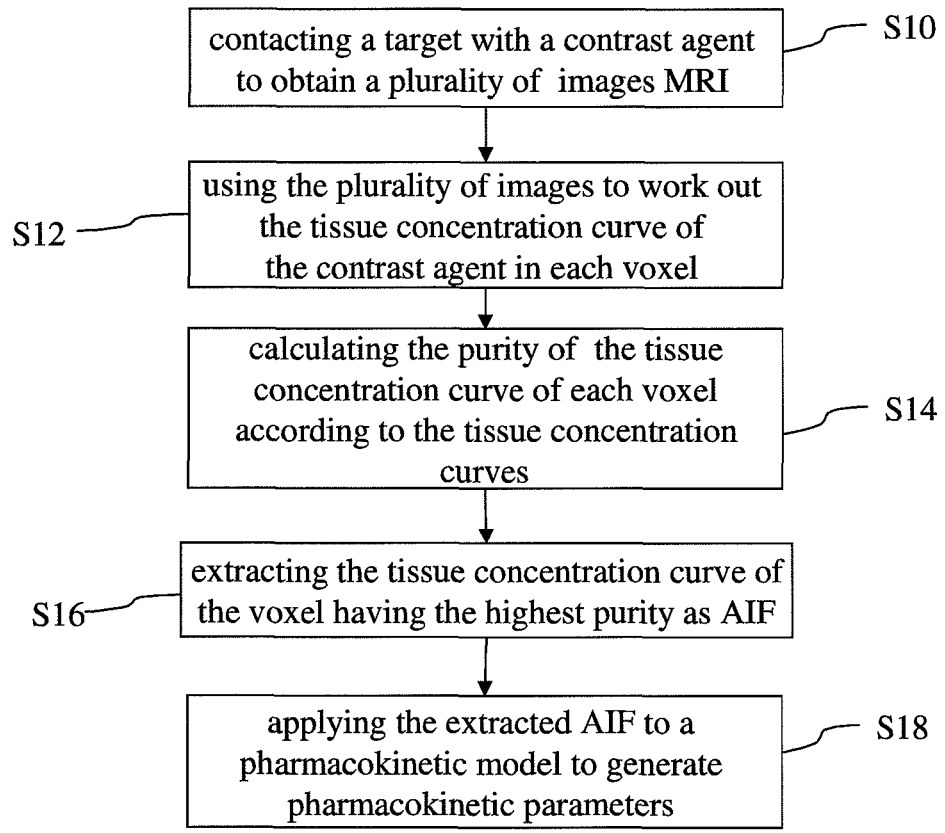
FIG. 2 shows a flowchart of DCE-MRI according to one embodiment of the present invention.

In one embodiment, the plurality of images are obtained via MRI. Refer to FIG. 2 showing a flowchart of DCE-MRI according to one embodiment of the present invention. In Step S18, apply the extracted AIF to a pharmacokinetic model, and use the AIF and the voxels corresponding to the time function to generate pharmacokinetic parameters. The pharmacokinetics correlates with the type of MRI. If MRI is the T1-weighted MRI, the pharmacokinetic parameters include the transfer rate constant ($K^{trans}$) from the intravascular system to the extravascular extracellular space (EES) or vice versa, the distribution volume (Ve) of the contrast agent in EES and the capillary plasma volume (Vp) of the contrast agent in EES. If MRI is the T2-weighted DSC-MRI (Dynamic Susceptibility Contrast MRI), the pharmacokinetic parameters include the cerebral blood flow (CBF), the cerebral blood volume (CBV), and the mean transit time (MTT). The obtained pharmacokinetic parameters can be used to diagnose vessel-related diseases or estimate the therapeutic effects of the vessel-related diseases, such as such as tumors and apoplexies.

If the plurality of images are obtained via PET, the pharmacokinetic parameters include the cerebral blood flow (CBF) and the cerebral oxygen metabolism rate (CMRO2).

Figure 3:
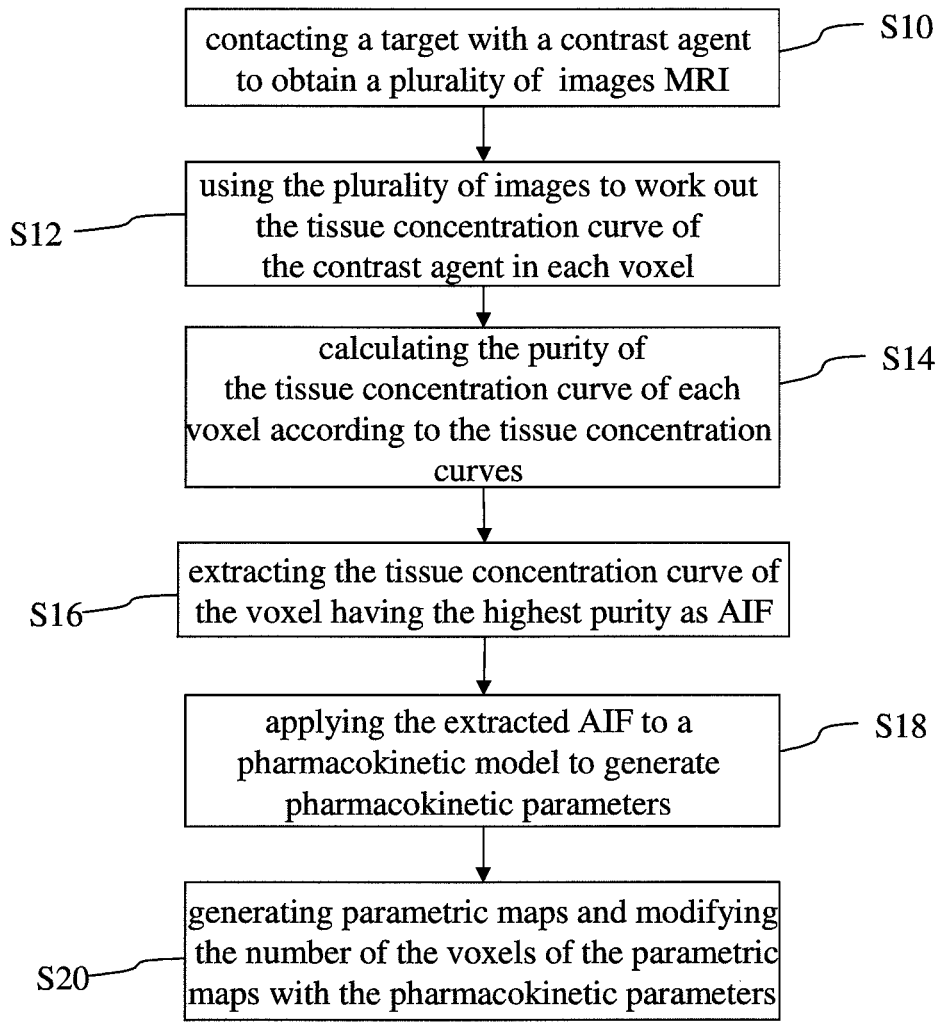
FIG. 3 shows a flowchart of DCE-MRI according to another embodiment of the present invention.

The abovementioned embodiments are the fundamental processes of the present invention. Refer to FIG. 3. In one embodiment, after Step S18 is further undertaken Step S20, which is a step of using the extracted AIF to generate parametric maps of pharmacokinetics, wherein the number of the voxels of the generated parametric maps are further modified with the pharmacokinetic parameters generated in Step S18. The other steps of this embodiment will not repeat herein because they are the same as the steps of the embodiment shown in FIG. 2.

The steps of the method of the present invention have been described above. Below, a set of equations are used to verify the present invention and prove the practicability thereof.

Herein, the plurality of T1-weighted DCE-MRI is used to demonstrate the present invention in detail. Firstly, the relationship between AIF and the pharmacokinetic parameters is described below. The time-dependent tracer (contrast agent) concentration variation in the voxels of the target tissue is expressed by Equation [1]:

$$C_t(t_k) = K^{trans} \sum_{n=1}^{k} \Delta t C_p(t_n) \times \exp[-k_{ep}(t_k - t_n)] + V_p C_p(t_k) \quad [1]$$

$$k = 1, \ldots, K,$$

wherein $C_p(t_k)$ is the tracer concentration in the blood plasma, e.g. the AIF; $C_t(t_k)$ is the tracer concentration in the tissue; $K^{trans}$ is the transfer rate constant from the intravascular system to the extravascular extracellular space (EES);

$$k_{ep}\left( = \frac{K^{trans}}{V_e} \right)$$

is the transfer rate constant from EES to the intravascular system; $V_p$ is the capillary plasma volume of the contrast agent in EES (per unit volume of tissue); $V_e$ is the distribution volume of the contrast agent in EES (per unit volume of tissue); $\Delta t$ is the temporal resolution; K is the total number of DCE-MRI image time series.

The notation is introduced to generalize Equation [1] for different voxels; for instance, $C_t(t_k,i)$ is the tracer concentration for time $t_k$ and voxel i, and $K^{trans}(i)$, $k_{cp}(i)$, $V_e(i)$ and $V_p(i)$ are the associated kinetic parameters for the voxel i. Note that the arterial input function $C_p(t_k)$ is independent of the voxel location. By collecting all the $C_t(t_1,i) \ldots C_t(t_K,i)$ into a K×1 vector and by letting $[[c_p=[C]]_p(t_1), \ldots, C_p(t_K)]^T$, the concentration time course from a voxel of interest can be given by Equation [2]:

$$x(i) = \begin{bmatrix} C_t(t_1, i) \\ \vdots \\ C_t(t_K, i) \end{bmatrix} = A(k_{ep}(i), c_p)s(i). \quad [2]$$

$$\text{wherein } s(i) = \begin{bmatrix} K^{trans}(i) \\ V_p(i) \end{bmatrix}$$

is a vector comprising the associated non-negative kinetic parameters, and $$A(k_{ep}(i), c_p) = \begin{bmatrix} \Delta t C_p(t_1) & C_p(t_1) \\ \sum_{n=1}^{2} \Delta t C_p(t_n) \times \exp[-k_{ep}(i)(t_2 - t_n)] & C_p(t_1) \\ \vdots & \vdots \\ \sum_{n=1}^{K} \Delta t C_p(t_n) \times \exp[-k_{ep}(i)(t_K - t_n)] & C_p(t_K) \end{bmatrix}$$

Suppose that AIF ($c_p$) can be further calculated more accurately. Then, for the kinetic parameters $k_{ep}(i)$, $K^{trans}(i)$, $V_p(i)$ with respect to all i's, the fitting problem of the non-negativity constrained curve in Equation [2] can be solved via the least squares method described by Equation [3]:

$$\min_{k_{ep}(i)\geq 0, s(i)\geq 0} \|x(i) - A(k_{ep}(i), \hat{c}_p)s(i)\|_2,  \quad [3]$$

wherein $\hat{c}_p$ denotes the calculated AIF, $\|\cdot\|_2$ the 2-norm operator, and $\geq$ component-wise inequality.

The relationship between AIF and kinetic parameters has been demonstrated above. Next, the present invention uses the BSS (Blind Source Separation) algorithm to automatically search for the voxel having the highest purity as the optimized AIF from a series of T1-weighted DCE-MRI data and identify the AIF as $c_p$. The purity of each voxel is defined by Equation [4]:

$$\rho_i = \frac{\|x(i)\|_2}{\|x(i)\|_1}, \quad [4]$$

wherein $\|\cdot\|_1$ is the 1-norm operator.

The purity measure $\rho_i$ is a reflection of the contribution from $c_p$ to x(i). The increased purity measure can be related to an increased contribution from $c_p$ in x(i). It can also be related to a reduced extent of partial volume contamination. AIF can be identified from the voxels x(i) via searching for a voxel whose purity measure is the maximum one, as shown in Equation [5]:

$$\hat{c}_p = x(i^*) \quad [5]$$

wherein $i^* = \arg_i \max \rho_i$. The selected voxel x(i*) corresponds to the voxel time course with minimal partial volume contamination and thus can be regarded as an AIF calculate. After the highest-purity AIF is obtained, Equations [1], [2] and [3] are used to work out pharmacokinetic parameters more definite and closer to the truth.

Figure 4A:
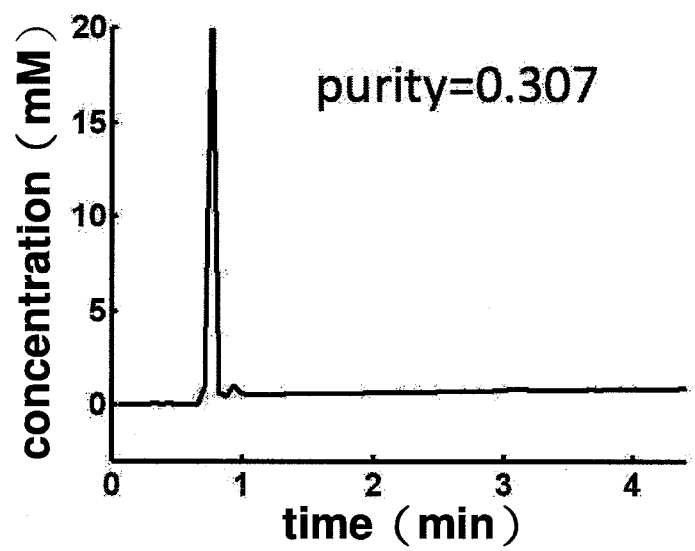
FIGS. 4(a)-4(f) respectively show the distribution shapes of the AIF by the method of the present invention and the AIFs selected manually.
Figure 4B:
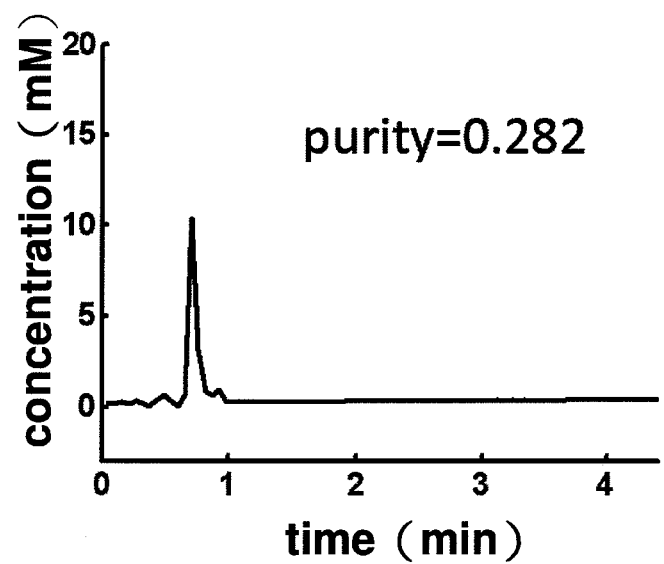
Figure 4C:
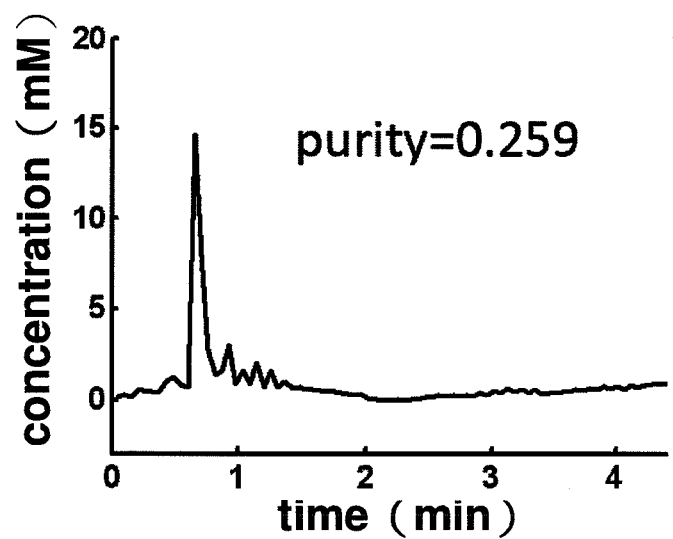
Figure 4D:
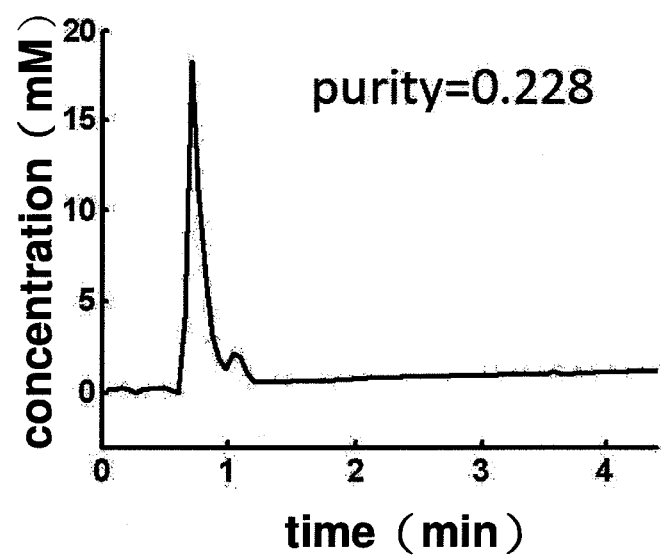
Figure 4E:
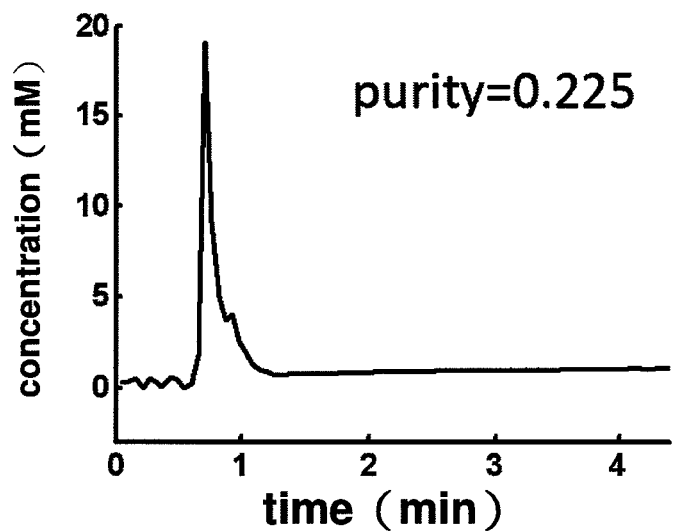
Figure 4F:
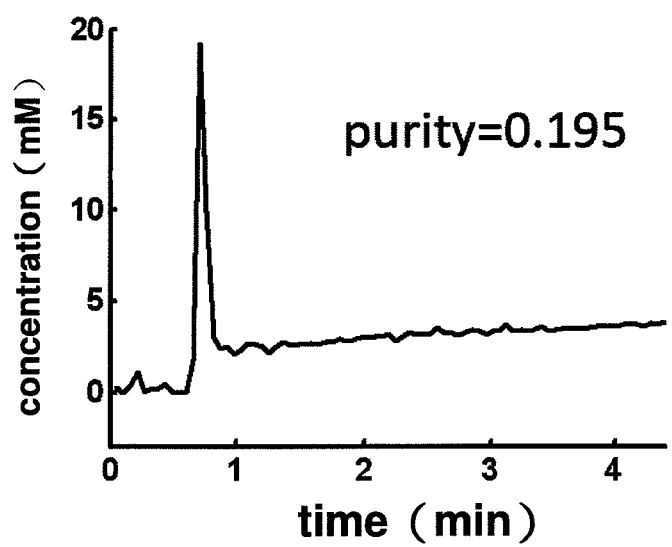
Figure 5A:
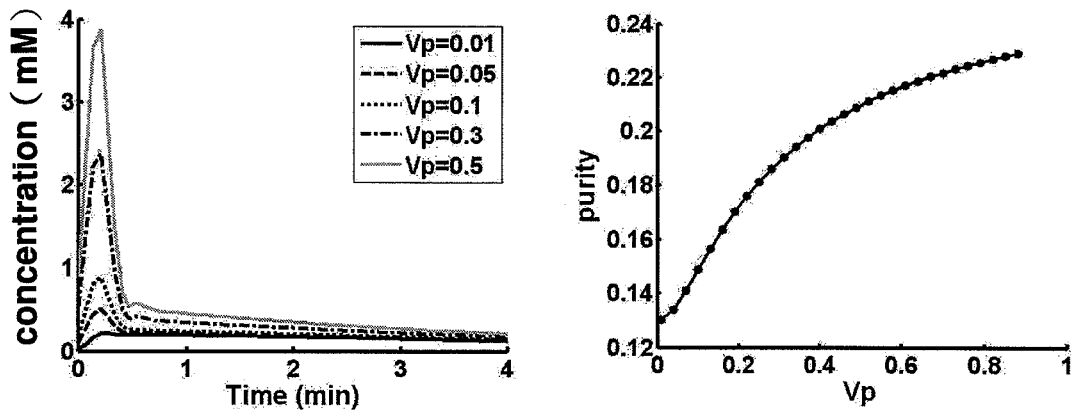
FIGS. 5(a)-5(c) respectively show the simulations of AIFs by varying kinetic parameters of the tissue time courses and the purities of the AIFs.
Figure 5B:
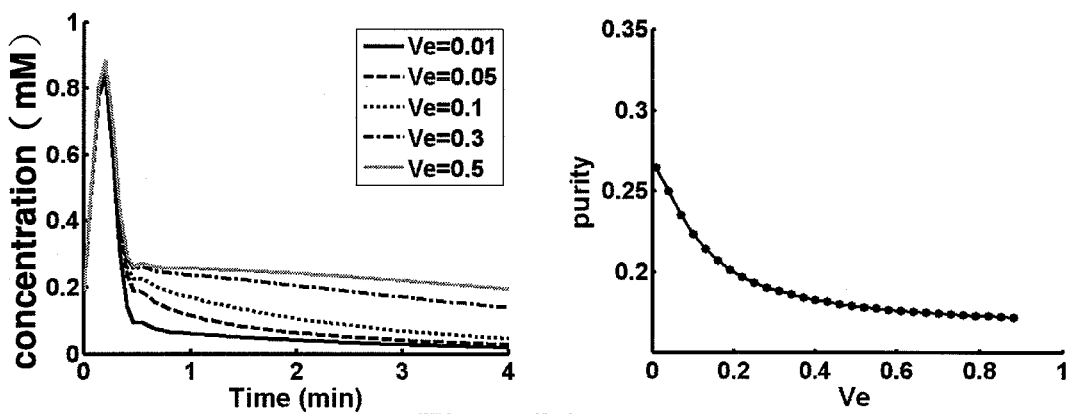
Figure 5C:
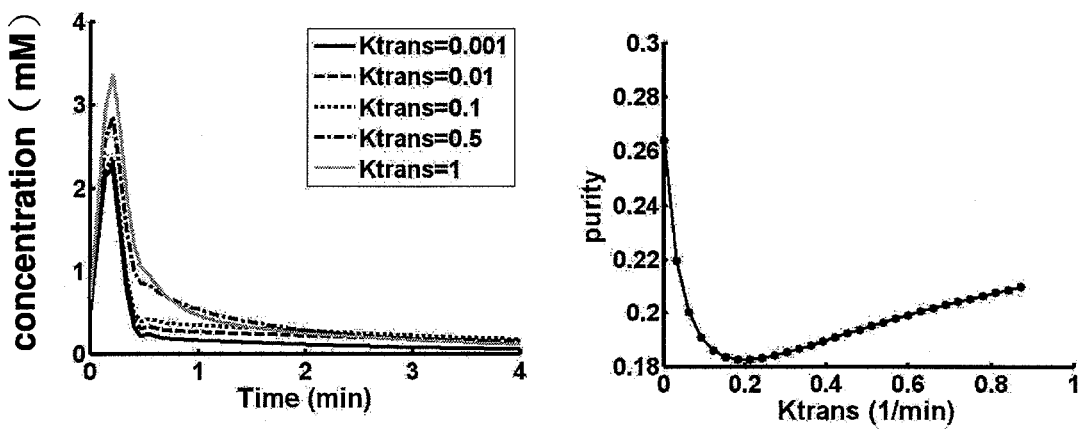

Refer to FIGS. 4(a)-4(f) respectively showing the distribution shapes of the AIF by the method of the present invention and the AIFs selected manually. FIG. 4(a) shows the distribution shape of the AIF obtained by the method of the present invention. FIGS. 4(b)-4(f) are the distribution shapes of the AIFs selected manually. From the above-mentioned distribution shapes, the facts are learned that the AIF by the method of the present invention has a pretty high purity and that the AIFs selected manually have relatively lower purities. The reduced purities of manually selected AIFs could be attributed to a decreased height of the peak (FIG. 4b), an elevated baseline of the curve (FIG. 4c), a broadening width in the first pass (FIG. 4d, FIG. 4e) or a drift of the returned baseline (FIG. 4f). Refer to FIGS. 5(a)-5(c) respectively showing the simulations of AIFs by varying kinetic parameters of the tissue time courses and the purities of the AIFs. FIG. 5(a) shows the curve obtained via varying $V_p$ with $V_e=0.3$ and $K^{trans}=0.1$. FIG. 5(b) shows the curve obtained via varying $V_e$ with $V_p=0.3$ and $K^{trans}=0.1$. FIG. 5(c) shows the curve obtained via varying $K^{trans}$ with $V_p=0.3$ and $V_e=0.3$. Thus, it is known that the pharmacokinetic parameters of the tissue could influence the tissue concentration curves and the calculated purities. The tracer concentration curve with a higher purity has a pointer shape. In other words, it is closer to an ideal impulse function.

Figure 6:
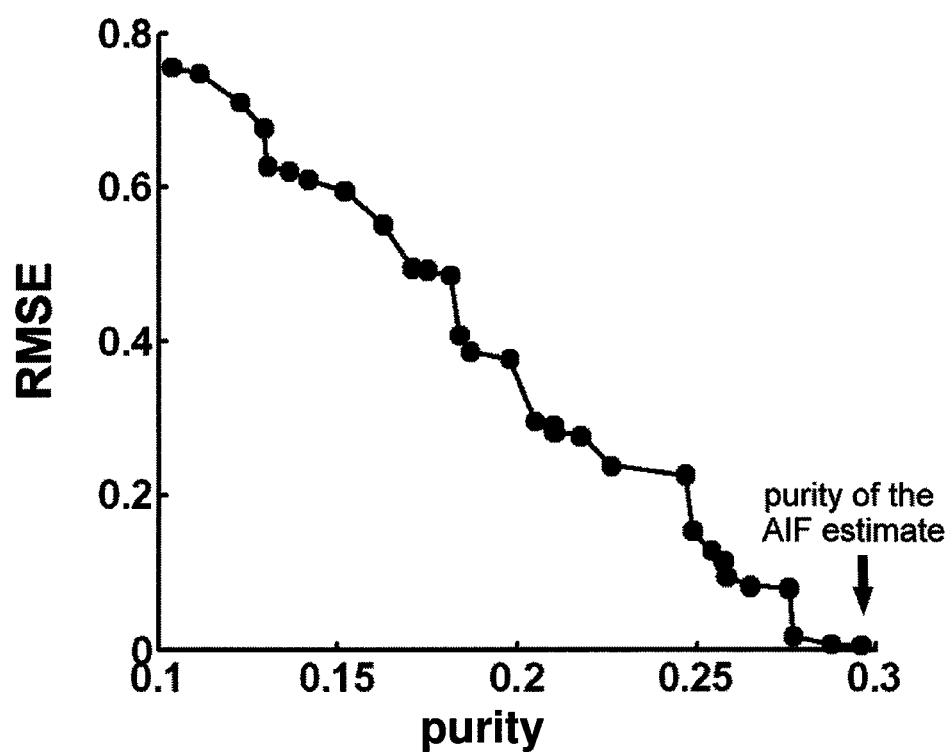
FIG. 6 shows the influence of the purity of AIF on RMSE between the ground-truth AIF and the tissue concentration curves with various purities.

Below are introduced computer simulations to prove that the AIF extracted by the present invention is closest to the ground-true AIF. Simulations are based on an assumption that a heterogeneous tissue has various concentration curves. The purity of each voxel is calculated. The ground-truth AIF is generated by using the modified population average AIF (Yang, Karczmar, et al. 2007). Next, a Monte-Carlo simulation is performed by using Equation [2] to create 100 tissue concentration curves x(i) with $K^{trans}(i)$ uniformly distributed between [0, 2.2] (min$^{-1}$), $V_e(i)$ [0, 1], and $V_p(i)$ [0, 1] respectively. The influence of purity level to the errors between the BSS-AIF and true-AIF is calculated as follows: thirty tissue concentration curves x(i) are randomly selected as the calculated AIFs whose purities vary from 0.104 to 0.296; the root-mean-square-error (RMSE) between the tissue concentration curve and the ground-truth AIF $c_p$ is measured. The results are shown in FIG. 6. The higher the purity, the smaller the RMSE.

Figure 7A:
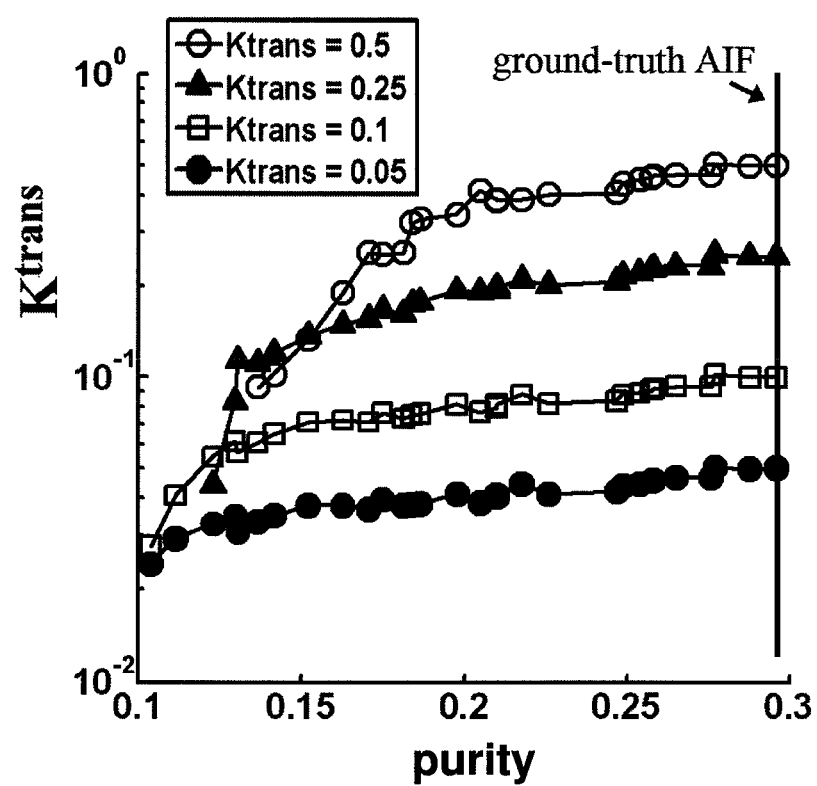
FIGS. 7(a)-7(c) show the influence of the purity of AIF on the calculated parameters.
Figure 7B:
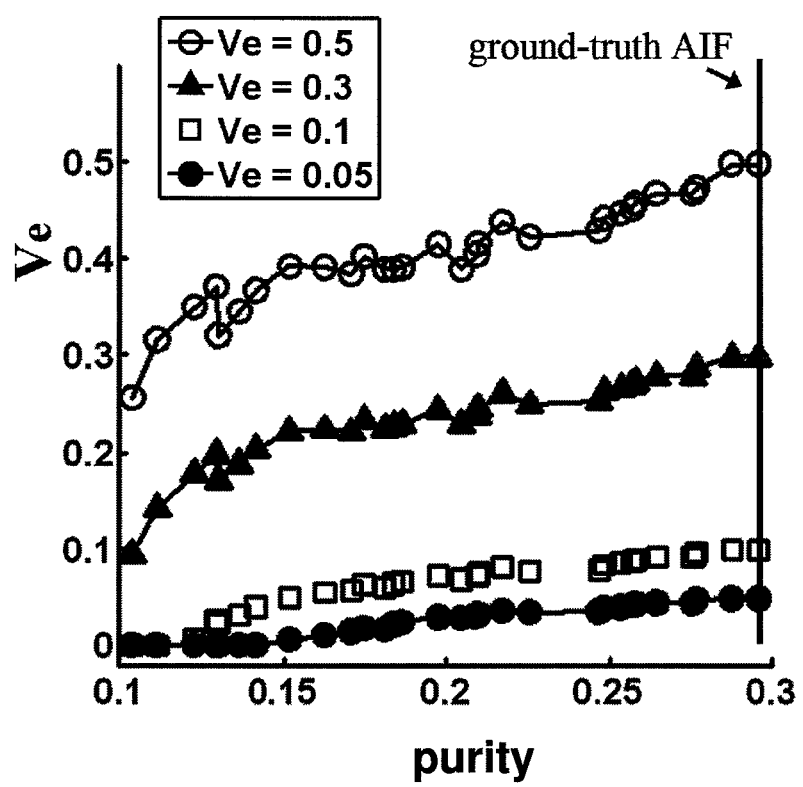
Figure 7C:
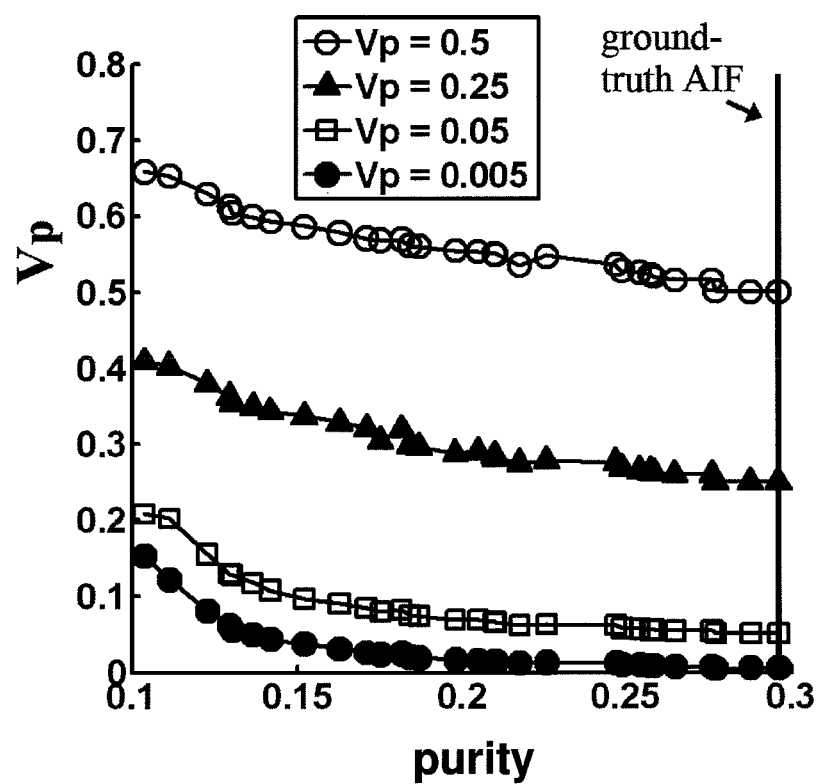

Next are calculated the influences of the purity of the calculated AIF on the derived kinetic parameters. The results are shown in FIGS. 7(a)-7(c). FIG. 7(a) shows the influence of the purity of the calculated AIF to the calculated $K^{trans}$, wherein $K^{trans}$ is in a logarithmic scale. FIG. 7(b) shows the influence of the purity of the calculated AIF to the calculated $V_e$, wherein $V_e$ is in a linear scale. FIG. 7(c) shows the influence of the purity of the calculated AIF to the calculated $V_p$, wherein $V_p$ is in a linear scale. The results show that a voxel having a lower purity causes underestimation of $K^{trans}$ and $V_e$ and overestimation of $V_p$.

In conclusion, the present invention uses the BSS algorithm to calculate the purities of voxels and automatically search for the voxel having the highest purity as the extracted AIF, which is closest to the ground-true AIF, whereby is improved the accuracy of the deduction of the quantitative indexes (pharmacokinetic parameters), and whereby is increased the efficiency of the quantitative analysis of DCE-MRI, and whereby is promoted the reliability of the derived indexes.

The embodiments described above are to demonstrate the technical thought and characteristics of the present invention to enable the persons skilled in the art to understand, make, and use the present invention. However, they are not intended to limit the scope of the present invention. Any equivalent modification or variation according to the spirit of the present invention is to be also included within the scope of the present invention.

What is claimed is:

1. A method for extracting an arterial input function, comprising steps:
   Step (a): contacting a target tissue with a contrast agent to obtain a plurality of images;
   Step (b): using said plurality of images to work out a time intensity curve of said contrast agent in each voxel;
   Step (c): using said time intensity curve to calculate a purity of said time intensity curve of each voxel; and
   Step (d): selecting said time intensity curve of a voxel having the highest purity in step (c) as an arterial input function,
   wherein calculating said purity ($\rho$) of said time intensity curve of each voxel by $$\rho = \frac{\|x(i)\|_2}{\|x(i)\|_1},$$

wherein $\|\cdot\|_1$ is the 1-norm operator, $\|\cdot\|_2$ is the 2-norm operator, and x(i) is the voxel.

2. The method for extracting an arterial input function according to claim 1, wherein said plurality of images are obtained via MRI (Magnetic Resonance Imaging).

3. The method for extracting an arterial input function according to claim 1, wherein said plurality of images are obtained via CT (Computed Tomography).

4. The method for extracting an arterial input function according to claim 3, wherein pharmacokinetic parameters derived from said time intensity images include cerebral blood flow (CBF), cerebral blood volume (CBV), and mean transit time (MTT).

5. The method for extracting an arterial input function according to claim 1, wherein said plurality of images are obtained via PET (Positron Emission Tomography).

6. The method for extracting an arterial input function according to claim 5, wherein pharmacokinetic parameters derived from said time intensity images include cerebral blood flow (CBF) and cerebral oxygen metabolism rate (CMRO2).

7. A method for dynamic contrast enhanced magnetic resonance imaging, comprising steps:

Step (a): contacting a target tissue with a contrast agent to obtain a plurality of images of magnetic resonance imaging;

Step (b): using said plurality of images to work out a tissue concentration curve of said contrast agent in each voxel;

Step (c): using said tissue concentration curve to calculate a purity of said tissue concentration curve of each voxel;

Step (d): extracting said tissue concentration curve of a voxel having the highest purity in step (c) as an arterial input function; and Step (e): applying said arterial input function extracted in Step (d) to a pharmacokinetic model to generate pharmacokinetic parameters, wherein calculating said purity ($\rho$) of said tissue concentration curve of each voxel by $$\rho = \frac{\|x(i)\|_2}{\|x(i)\|_1},$$

wherein $\|\cdot\|_1$ is the 1-norm operator, $\|\cdot\|_2$ is the 2-norm operator, and $x(i)$ is the voxel.

8. The method for dynamic contrast enhanced magnetic resonance imaging according to claim 7, wherein said tissue concentration curve of said contrast agent is generated via recording time-dependent variation of a concentration of said contrast agent in each voxel of said plurality of images.

9. The method for dynamic contrast enhanced magnetic resonance imaging according to claim 7, wherein said magnetic resonance imaging (MRI) is T1-weighted MRI or T2-weighted DSC-MRI (Dynamic Susceptibility Contrast MRI).

10. The method for dynamic contrast enhanced magnetic resonance imaging according to claim 9, wherein said magnetic resonance imaging (MRI) is T1-weighted MRI, and wherein said pharmacokinetic parameters include a transfer rate constant from an intravascular system to an extravascular extracellular space (EES), a distribution volume of said contrast agent in EES, and a capillary plasma volume of said contrast agent in EES.

11. The method for dynamic contrast enhanced magnetic resonance imaging according to claim 9, wherein said magnetic resonance imaging (MRI) is T2-weighted DSC-MRI, and wherein said pharmacokinetic parameters include cerebral blood flow (CBF), cerebral blood volume (CBV), and mean transit time (MTT).

12. The method for dynamic contrast enhanced magnetic resonance imaging according to claim 7 further comprising a step of generating parametric maps of pharmacokinetics.

13. The method for dynamic contrast enhanced magnetic resonance imaging according to claim 12, wherein said pharmacokinetic parameters are calculated from said tissue concentration curve of each voxel and said arterial input function.

* * * * *